United States Patent
Pujado (12)

(10) Patent No.: US 6,768,013 B1
(45) Date of Patent: Jul. 27, 2004

(54) INTRINSICALLY SAFE OXIDATION PROCESS

(75) Inventor: Peter R. Pujado, Kildeer, IL (US)

(73) Assignee: UOP LLC, Des Plaines, IL (US)

( * ) Notice: Subject to any disclaimer, the term of this patent is extended or adjusted under 35 U.S.C. 154(b) by 234 days.

(21) Appl. No.: 09/882,519

(22) Filed: Jun. 15, 2001

(51) Int. Cl.$^7$ ............................................. C07D 301/12
(52) U.S. Cl. ...................... 549/531; 423/584; 423/659; 540/536; 549/248; 549/273; 549/295; 549/523; 549/533; 560/243; 560/245; 562/412; 562/415; 564/267; 568/471; 568/475; 568/476; 568/802; 568/803
(58) Field of Search .................. 423/584, 659, 423/531, 523; 549/273, 295, 533, 248; 568/802, 803, 475, 476, 471; 564/267; 540/536; 562/412, 415; 560/243, 245

(56) References Cited

U.S. PATENT DOCUMENTS

| | | | |
|---|---|---|---|
| 4,212,772 A | | 7/1980 | Mross et al. ................. 252/476 |
| 4,336,240 A | | 6/1982 | Moseley et al. ............. 423/584 |
| 4,347,231 A | | 8/1982 | Michaelson .................. 423/584 |
| 4,369,128 A | * | 1/1983 | Moseley et al. ............. 423/584 |
| 4,532,362 A | * | 7/1985 | Kukes et al. ................ 568/475 |
| 4,832,938 A | | 5/1989 | Gosser et al. ................ 423/584 |
| 5,925,588 A | | 7/1999 | Chuang et al. .............. 502/181 |
| 6,042,804 A | | 3/2000 | Huckins ...................... 423/584 |

FOREIGN PATENT DOCUMENTS

JP   234550   * 10/1987

OTHER PUBLICATIONS

Abstract of Japanese 62–234550 Published Oct. 14, 1987.*

* cited by examiner

*Primary Examiner*—Wayne A. Langel
(74) *Attorney, Agent, or Firm*—John G. Tolomei; Frank S. Molinaro; Arthur E. Gooding

(57) ABSTRACT

A novel process for the direct oxidation of hydrogen and hydrocarbons is disclosed, where the explosion risks inherent in gas phase oxidations are substantially eliminated. Gaseous oxidation reactants are soluble in a first reaction solvent phase such as a perfluorocarbon (e.g. $C_8F_{18}$) and the oxidation product is preferentially soluble in a second product solvent phase such as water or a dilute acid. A solid catalyst such as palladium on alumina is then contacted with the dissolved reactants. The oxidation product such as hydrogen peroxide may be separated from the reaction solvent phase by extraction into the immiscible product solvent phase and then separated from it by distillation, thereby allowing re-use of the aqueous phase. The present invention may be carried out using a two-phase reaction system whereby both the reaction solvent and product solvent are contained within a reaction vessel into which the solid catalyst is slurried and mechanically agitated to promote the reaction.

23 Claims, 1 Drawing Sheet

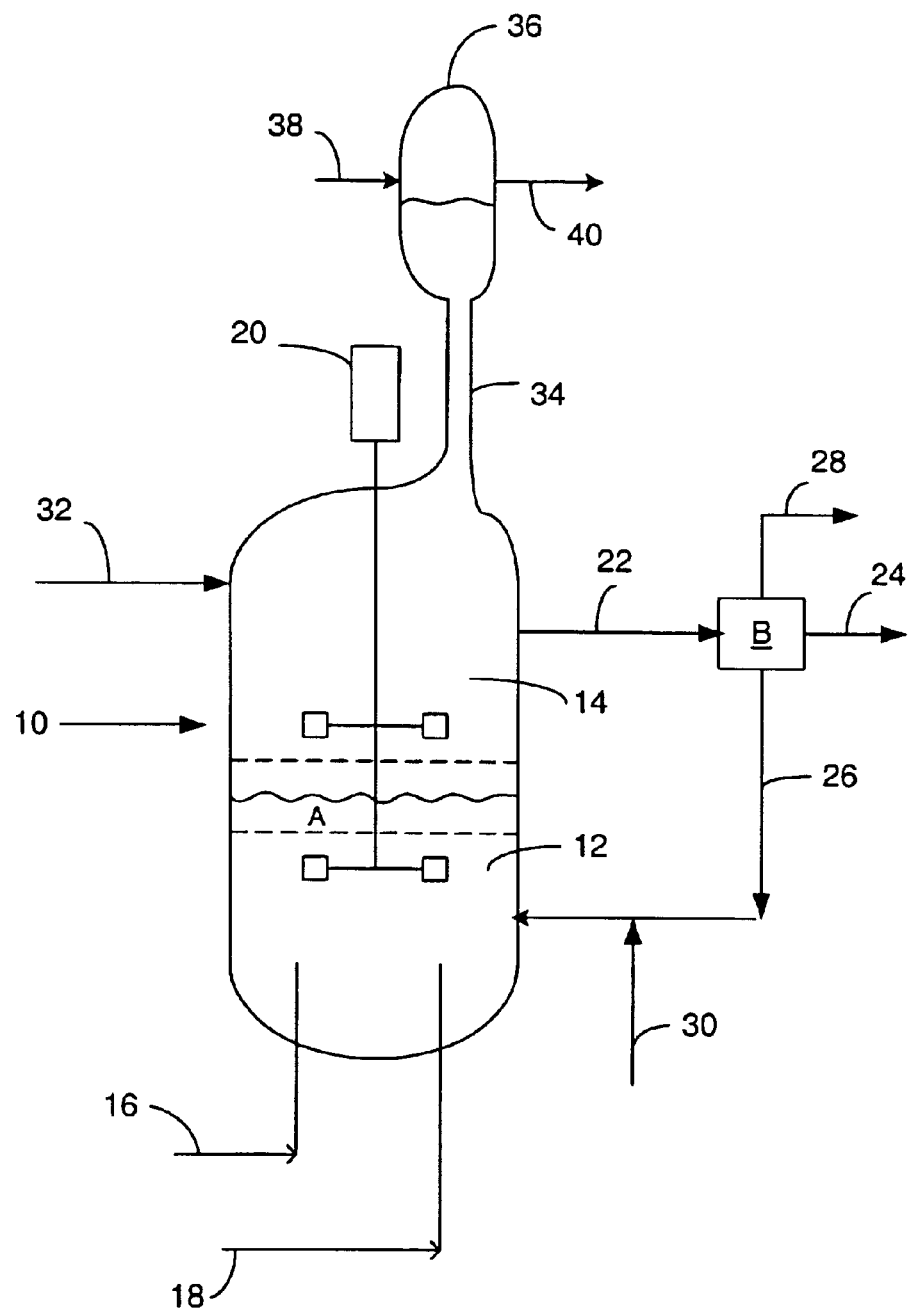

INTRINSICALLY SAFE OXIDATION PROCESS

FIELD OF THE INVENTION

The present invention relates to a novel process for performing oxidation reactions, especially those where the direct contact of reactants presents an explosion hazard. The invention overcomes this risk by dissolving a feed component and an oxidizing agent (e.g. oxygen gas) in solution prior to reaction. The process is especially useful for the direct contacting of hydrogen and oxygen to yield hydrogen peroxide.

BACKGROUND OF THE INVENTION

Currently the most widely practiced industrial scale production method for hydrogen peroxide is an indirect reaction of hydrogen and oxygen employing alkylanthraquinone as the working material. In a first catalytic hydrogenation step, the alkylanthraquinone, dissolved in a working solution comprising organic solvents (e.g. di-isobutylcarbinol and methyl naphthalene), is converted to hydroalkylanthraquinone. In a separate autoxidation step, this reduced compound is oxidized to regenerate the alkylanthraquinone and yield hydrogen peroxide. Subsequent separation by aqueous extraction, refining, and concentration operations are then employed to give a merchant grade product.

Overall, this indirect route to $H_2O_2$ formation, whereby a carrier medium is reduced and then oxidized, adds complexity and requires high installation and operating costs. One notable drawback is the significant solubility of the alkylanthraquinone in the aqueous extraction medium used to separate the hydrogen peroxide product. This promotes loss of working solution and leads to contamination of the hydrogen peroxide product with organic species that, when the hydrogen peroxide is concentrated to levels suitable for transport, are reactive with it. A second problem relates to the solubility of the aqueous extraction solution in the alkylanthraquinone working solution. When wet working solution is separated from the aqueous phase for recycle to the indirect oxidation stage, residual aqueous phase "pockets" within the organic solution provide regions for hydrogen peroxide product to concentrate to the extent of becoming hazardous.

Considerably more simple and economical than the alkylanthraquinone route is the direct synthesis of hydrogen peroxide from gaseous hydrogen and oxygen feed streams. This process is disclosed in U.S. Pat. No. 4,832,938 B1 and other references, but attempts at commercialization have led to industrial accidents resulting from the inherent explosion hazards of this process. Namely, explosive concentrations of hydrogen in an oxygen-hydrogen gaseous mixture at normal temperature and pressure are from 4.7–93.9% by volume. Thus the range is extremely broad.

It is also known that dilution of the gaseous mixture with an inert gas like nitrogen scarcely changes the lower limit concentrations, on an inert gas-free basis, of the two gases. Within normal ranges of pressure variation (1–200 atmospheres) and temperature variation (0–100° C.) the explosive range is known to undergo little change. Furthermore, even when these reactants are brought together in a ratio that, in the homogeneous condition, would be outside the flammability envelope, the establishment of homogeneity from pure components necessarily involves at least a temporary passage through the flammability envelope. For these reasons, the explosion risks associated with the direct contacting of hydrogen and oxygen are not easily mitigated In the area of directly contacting hydrogen and oxygen, some efforts have also been made to contain the reaction in a liquid phase. For example, U.S. Pat. No. 5,925,588 B1 discloses the use of a catalyst having a modified hydrophobic/hydrophilic support to provide optimum performance in an aqueous liquid phase. Also, U.S. Pat. No. 6,042,804 B1 discloses dispersing minute bubbles of hydrogen and oxygen into a rapidly flowing acidic aqueous liquid medium containing a catalyst Unfortunately, however, the hydrogen and oxygen reactants are only slightly soluble in the aqueous reaction solvents disclosed in these references.

Other references, namely U.S. Pat. No. 4,336,240 B1 and U.S. Pat. No. 4,347,231 B1 disclose two-phase reaction systems with a homogeneous catalyst dissolved in an organic phase. As mentioned in the former of these two references, homogeneous catalyst systems in general suffer from drawbacks that are a deterrent to their commercial use. The adverse characteristics include poor catalyst stability under reaction conditions, limited catalyst solubility in the reaction medium, and low reaction rates for the production of hydrogen peroxide. In addition, a gaseous $H_2/O_2$ containing environment above the two-phase liquid reaction system maintains the equilibrium concentrations of these reactants dissolved in the liquid phase. Therefore, this gaseous atmosphere above the reaction liquid must necessarily be outside the flammability envelope, thus greatly restricting the range of potential reactant mole ratios in the liquid phase.

In contrast to the prior art, the present invention overcomes to a large extent the hazards associated with the direct reaction of hydrogen and oxygen by dissolving these reactant gases into a reaction solvent (e.g. perfluorooctane) in which they are highly soluble. The present invention also relies on heterogeneous reaction chemistry. When hydrogen and oxygen are combined, the product hydrogen peroxide migrates into an aqueous phase, also present in the reaction mixture, from which this product is recovered due to its preferential solubility in this phase.

Several advantages over conventional alkylanthraquinone technology are associated with the present invention. The reaction solvent (e.g. perfluorooctane) dissolves water to a very limited extent, typically less than 30 ppm at saturation and under reaction conditions. Likewise, only minute amounts of reaction solvent are dissolved in the aqueous, or product solvent, phase. Furthermore, the present invention avoids a gaseous environment containing any significant quantities of reactants above the liquid reaction system. This is achieved by feeding reactants directly to the reaction solvent and, above the liquid reaction system, sweeping any unreacted components and contaminants with an inert gas such as nitrogen from the reaction environment.

The realization of a commercially viable direct synthesis of hydrogen peroxide provides a considerable cost savings over the above mentioned indirect alkylanthraquinone route. Furthermore, the direct method of the present invention overcomes the inherent explosion hazards associated with contacting hydrogen and oxygen in the gas phase. The cheaper route to hydrogen peroxide disclosed by applicant also favorably impacts the economics of downstream uses, such as in the further reaction of hydrogen peroxide with propylene to form propylene oxide.

While the synthesis of hydrogen peroxide is of primary interest, the present invention is suitable for a number of oxidative and combustive reactions where an explosion potential exists, for example the conversion of ethylene and oxygen to ethylene oxide, as described in U.S. Pat. No. 4,212,772 B1.

SUMMARY OF THE INVENTION

The present invention is a process for the liquid-phase oxidation of hydrogen and hydrocarbons that overcomes inherent explosion hazards associated with directly mixing reactants (e.g. hydrogen and oxygen) in the gas phase. Also, the invention is simpler and cheaper than commercially employed indirect oxidation routes, such as those involving the use of an alkylanthraquinone intermediate to facilitate the overall conversion of hydrogen and oxygen to hydrogen peroxide. The present invention is associated with the realization that certain liquids are capable of dissolving oxygen in concentrations significant enough that hydrogen peroxide and other oxidized products can be synthesized at commercially competitive rates in the liquid phase. Furthermore, immiscible solvents for the reactants and products are used as a means of easily extracting oxidized species preferentially into a product solvent. Extraction of the oxidized product may occur within the reactor simultaneously with the oxidation reaction or it may be a separate step after the oxidation reaction. In the former case, a two-phase liquid reaction environment, into which a solid catalyst is dispersed, is preferably used to effect the oxidation reaction of the present invention.

In one embodiment, therefore, the present invention is a process for oxidizing a feed component with an oxidizing agent, the process comprising dissolving the feed component and an oxidizing agent comprising oxygen in a reaction solvent selected from the group consisting of fluorocarbons, chlorofluorocarbons, hydrochlorofluorocarbons, fluorine-substituted oxygenated hydrocarbons, and mixtures thereof, and thereafter reacting the feed component and the oxidizing agent in the presence of a solid oxidation catalyst and under effective oxidation conditions to yield an oxidized product that is preferentially soluble in a product solvent compared to the reaction solvent.

In a preferred embodiment, the present invention is a process as described above where the reaction solvent, the solid oxidation catalyst, and the product solvent are contained in an oxidation reactor, and the reaction solvent and product solvent are present as separate liquid phases.

In a second embodiment, the present invention is a process for producing an oxidized product, where the process comprises dissolving a feed component and an oxidizing agent in a reaction solvent selected from the group consisting of fluorocarbons, chlorofluorocarbons, hydrochlorofluorocarbons, fluorine-substituted oxygenated hydrocarbons, and mixtures thereof. The process further comprises reacting the dissolved feed component and oxidizing agent in a reaction zone under effective oxidation conditions and in the presence of a solid oxidation catalyst to yield an oxidation product. The process further comprises extracting the oxidation product into a product solvent in which the oxidation product is preferentially soluble. The process further comprises separating the oxidation product and residual amounts of the reaction solvent in the product solvent from the product solvent to yield a regenerated product solvent, a purified oxidation product, and a recovered reaction solvent and recycling the recovered reaction solvent to the reaction zone.

In a preferred embodiment, the present invention is a process as described in the second embodiment, where the steps of dissolving, reacting, and extracting occur within the reaction zone containing the reaction solvent and product solvent as separate liquid phases.

These and other embodiments will be clarified in the following detailed description of the invention.

BRIEF DESCRIPTION OF THE DRAWING

The drawing shows, schematically, one possible embodiment of the reaction system of the present invention, as employed specifically for the synthesis of hydrogen peroxide from hydrogen and oxygen. This drawing is intended only to illustrate the invention without limiting its broad scope as set forth in the appended claims.

DETAILED DESCRIPTION OF THE INVENTION

As mentioned, the invention relates to an improved method for oxidizing a feed stream that overcomes complexities and safety concerns associated with methods of the prior art. The process comprises dissolving a feed component and an oxidizing agent in one liquid phase or reaction solvent, within a reaction system and contacting the dissolved reactants under effective oxidation conditions with a solid oxidation catalyst present in the reaction mixture.

The feed and oxidizing agent may be dissolved in the reaction solvent in any order or fed simultaneously in separate streams to the reaction solvent. For example, it is possible to dissolve oxygen in the reaction solvent to saturation and subsequently contact the resulting oxygen-saturated reaction solvent with a hydrogen stream, such as in a tubular mixer. Using the reaction solvents described later, the hydrogen solubility is generally affected to only a minor extent by the presence of oxygen in the reaction solvent.

In another embodiment, the potential for gas-phase contacting of reactants may also be eliminated by dissolving oxygen in a first portion of the reaction solvent and dissolving hydrogen or the hydrocarbon species to be oxidized in a second portion of the reaction solution. In this case, the dissolution steps may be carried out, for example, in separate stirred tanks before mixing the portions of reaction solvent. Thus, it is not necessary that the dissolution of the reactants into the reaction solvent occur within the reaction vessel. It is certainly possible that reaction solvent containing previously dissolved reactants be passed through a fixed bed of catalyst or reacted in a slurry reactor. Likewise, extraction of the oxidized product into a product solvent may occur in a separate phase within the reactor or in a different vessel outside of the reactor. In the former case, when a two-phase reaction system is employed, the solid oxidation catalyst may be present in the reaction mixture as a slurry, or it may be physically isolated in the region of the reaction solvent/product solvent interface using, for example, wire mesh baskets.

Preferably, the two liquid phases and the solid oxidation catalyst are present in a reaction vessel. In this embodiment, mechanical agitation (e.g. stirring, shaking, vibrating, etc.) is used to effect not only the contacting between the catalyst and reactants, but also between the two phases in the reaction system. The latter contacting is important for allowing diffusion of the oxidized reaction product into the product solvent phase, in which the oxidized product is preferentially soluble. By preferentially soluble is meant that, at equilibrium, the ratio of the concentration of the oxidized reaction product in the aqueous phase to that in the organic phase is greater than 1. By being preferentially soluble in the aqueous phase, the oxidized product is extracted from the reaction solvent and thus easily removed from the reactor. Although the interface between the phases of the reaction and product solvents may become emulsified due to vigorous mixing, well-defined phases can nevertheless exist in quiescent zones removed from this interface. Generally, the reaction product is withdrawn from such a quiescent zone in the product solvent phase.

The present invention is particularly applicable to processes where a potential for explosion exists when the feed and oxidizing agent are mixed directly. For example, it is well known that mixtures of hydrogen and oxygen, in a broad range of relative concentrations defining the flammability envelope, can explode in the presence of an ignition source, such as a spark. Such mixtures, however, when reacted catalytically and under controlled conditions will ideally not spontaneously combust but form the commercially desired end product hydrogen peroxide. Of course, reaction conditions such as temperature and residence time can be adjusted to maximize the yield of hydrogen peroxide and minimize the formation of water.

To reduce the possibility of explosion, it is of course possible to also directly mix hydrogen and oxygen in a non-explosive ratio, or outside of the flammability envelope. However, such ratios are far from the stoichiometric 1:1 molar ratio in which these reactants are consumed, thus requiring either a large recycle or waste of the non-limiting reactant. For example, when this mode of operation is used, it is preferable that hydrogen and oxygen are mixed continuously in a proportion of about 3% hydrogen by volume and about 97% oxygen by volume. Furthermore, while hydrogen/oxygen mixtures generally having less than about 4.7% hydrogen by volume are non-explosive, the establishment of this mixture from pure components always includes a transient period where at least some of the reactants are within the flammability envelope and pose an explosion hazard. Thus, the possibility for an explosive reaction mixture exists, regardless of the fact that the homogeneous reaction mixture is outside the flammability envelope.

Without being bound to any particular theories, two mechanisms, free radical formation and insufficient heat dissipation, are typically used to explain explosivity. Free radical formation and propagation as a description for runaway of the reaction system was described by Semenov and more recently by Maas and Warnatz. Walls of channels wherein explosions may occur are considered "third bodies" that quench the reaction by neutralizing the radicals. The second theory, pioneered by Frank-Kamenetsky, compares the heat release to the heat removal potential.

Consistent with both of these theories, it is known that mixing hydrogen and oxygen is made less hazardous when performed in the presence of fine sand that disperses these gases within interstitial voids surrounded by solid particles that adsorb heat and/or free radicals. Thus, commercial attempts at directly contacting hydrogen and oxygen to form hydrogen peroxide have utilized this technique to avoid potential detonation upon passing gaseous mixtures from pure components through the flammability envelope and finally to a homogeneous, non-explosive mixture.

Taking this concept to its maximum logical extent, dissolution of gaseous reactants into a liquid solution disperses them even more finely. In this case, reactants are actually distributed within the reaction solvent at the molecular level. Thus, applicant has found that the use of a liquid solvent can essentially eliminate the explosion potential between dissolved reactants. Specifically, the surrounding liquid is a medium for absorbing the heat released and/or free radicals formed that would otherwise propagate an explosive reaction. In contrast, gaseous diluents do not provide nearly the same heat absorption capacity. Also, physical mixing with a gaseous diluent generally results in transient or localized non-homogeneous reactant concentrations, in contrast to the dispersion at the molecular level that occurs upon dissolution of reactant gases. Furthermore, subsequent separations involving gaseous components often result in considerable expense.

An additional characteristic of the process of the present invention that overcomes the inherent hazards associated with explosive reaction mixtures is a gaseous environment above the liquid reaction mixture that is substantially free of feed components and oxygen. By substantially free is meant that, preferably, the sum of the concentrations of the feed component and oxygen in the gaseous environment above the reaction mixture is less than about 1% by volume. The substantial absence of explosive species in the gaseous reaction environment above the liquid-phase reaction zone is maintained through directly dissolving the feed component and oxygen in the reaction liquid and continually sweeping any unreacted gases and contaminant gases exiting the liquid phase with a purge stream. This purge stream preferably comprises a noble gas (e.g. helium) or an otherwise inert gas selected from the group consisting of nitrogen, carbon dioxide, and mixtures thereof. Thus, the present invention avoids the need for any type of gaseous environment containing substantial quantities of hydrogen or other feed components and oxygen.

Many types of oxidation reactions involve mixing potentially explosive reactant/oxidizing agent combinations. For example, specific oxidation reactions for which the mixing/reaction process of the present invention is suited include, but are not limited to, the direct synthesis of hydrogen peroxide from hydrogen and oxygen, as described in U.S. Pat. No. 4,832,938 B1 and the production of ethylene oxide from ethylene and oxygen, as described in U.S. Pat. No. 4,212,772 B1. Other applicable processes include, but are not limited to, the oxidation of methane to methanol and/or formaldehyde; the oxidation of ethane to acetic acid; the oxidation of ethylene to vinyl acetate; the oxidation of propane or propylene to acrolein, a precursor to acrylic acid; the oxidation of n-butane to maleic anhydride; the oxidation of isobutane, isobutylene, or tertiary butyl alcohol to methacrolein, a precursor to methacrylic acid; the oxidation of orthoxylene to phthalic anhydride; the oxidation of metaxylene to isophthalic acid; and the oxidation of paraxylene to terephthalic acid.

In the case of the above oxidation reactions where hydrocarbons are feed components, oxidation catalysts, for example silver on alumina, may be used. In contrast, the reaction of hydrogen and oxygen generally occurs in the presence of a reduction or hydrogenation catalyst such as palladium on alumina While this reaction may therefore be more accurately referred to as the reduction of oxygen, for the sake of simplicity in this disclosure the reaction of hydrogen and oxygen to form hydrogen peroxide will be categorized as an oxidation reaction. Thus, this reaction will be deemed in same general class as those mentioned above where hydrocarbons are used as reactants and traditional oxidation catalysts are employed.

The feed stream to the process of the present invention therefore broadly comprises a feed component that is hydrogen or a hydrocarbon. In view of the above reactions for which the present invention is specifically applicable, the feed component comprises hydrogen or a hydrocarbon selected from the group consisting of methane, ethane, ethylene, propane, propylene, n-butane, isobutane, isobutylene, tertiary butyl alcohol, orthoxylene, metaxylene, paraxylene, and mixtures thereof. The feeds may be available as pure components, or they may be commercial streams containing other species not necessarily involved in the oxidation reaction. For example, a commercial ethylene stream may contain methane, ethane, hydrogen, and other impurities that will not significantly impact the utility of this feed stream for the production of ethylene oxide. The oxidizing agent is preferably oxygen, either in its pure form or any convenient impure form, such as air.

The reaction solvent used in the present invention is characterized in that it has a high solubility of oxygen as well as hydrogen or the hydrocarbon feed component used as an oxidation reactant. Reaction solvents comprising fluorocarbons, chlorofluorocarbons, and hydrochlorofluorocarbons are especially useful because their oxygen solubility limits represent, in some cases, higher oxygen concentrations on a mole/liter basis than found in air. In fact, the oxygen solvency capability of these materials has led to investigation of their use as blood substitutes. It has also been demonstrated that a small animal (e.g. a mouse) can easily survive while immersed in oxygen-saturated chlorofluorocarbons or hydrochlorofluorocarbons for extended periods of time. The potential reaction solvents also extend to flourine-substituted oxygenated hydrocarbons (e.g. perfluorinated alcohols, ethers, or ketones), where at least one alkyl hydrogen of the homologous oxygenate is substituted for fluorine. Preferred reaction solvents are the completely fluorine-substituted $C_5$–$C_8$ hydrocarbons (e.g. perfluorohexane) due to their extraordinary oxygen solvency, high density, hydrophobicity (i.e. tendency to form a separate phase in the presence of an aqueous solution), and low volatility. These liquids are available from commercial suppliers under various trade names, such as 3M™ Performance Fluids (Minneapolis, Minn.).

In terms of oxygen solubility, reaction solvents capable of dissolving greater than about 50 ml of oxygen per 100 ml of reaction solvent at 1 atmosphere and 25° C. are preferred. In most cases, the solubility of other gases (e.g. hydrogen) within the reaction solvent is hardly affected by the degree of saturation of the reaction solvent with oxygen. The ability of the reaction solvent to phase separate from the preferred aqueous product solvent phase is based to some extent on the density of the reaction solvent, which is ideally significantly different from that of water at ambient temperature. Thus, it is preferred that the density of the reaction solvent is greater than about 1.5 g/ml at 25° C.

Finally, it is preferred that an excellent separation between the preferred aqueous product solvent and the reaction solvent can be obtained so that problems analogous to the previously mentioned difficulties associated with cross contamination of the working solution and extraction phases in the alkylanthraquinone process are avoided. Therefore, it is preferred that the solubility of water in the product solvent is less than about 50 ppm at 25° C. In terms of meeting these preferred ranges for oxygen solubility, density, and hydrophobicity, the above-mentioned $C_5$–$C_8$ perfluoroalkanes are suitable.

Aqueous solutions (e.g. water) are preferred for the product solvent, in view of the need to phase separate it from the reaction solvent. It may be desirable to adjust the pH of the product solvent to enhance the overall system performance. For example, when the oxidation product is hydrogen peroxide, it is preferable that the product solvent is acidified.

Suitable oxidation catalysts generally comprise a metal dispersed on a solid support, where synthesis details are well known in the art. Preferably, the metal is selected from the group consisting of Au, Ag, Pt, Pd, Ir, Rh, Hg, Ru, Os, and mixtures thereof. The solid support is preferably selected from the group consisting of inorganic refractory metal oxides (e.g. silica and alumina), carbon, and polymers (e.g. polytetraflouroethylene). The heterogeneous reaction, where the catalytic metal is affixed to a solid support, overcomes the difficulties of homogeneous systems associated with the loss of catalytic metal, limited catalyst solubility, and/or metal precipitation.

As mentioned, a particular application for the oxidation process of the process of the present invention is in the production of hydrogen peroxide directly from hydrogen and oxygen. Effective conditions appropriate for this reaction include a temperature from about 0° C. to about 90° C., an absolute pressure from about 1 to about 200 atmospheres, and a gas hourly space velocity from about 50 to about 50,000 $hr^{-1}$. As is understood in the art, the gas hourly space velocity is the volumetric hourly feed rate of gaseous components, at standard conditions, to the reactor divided by the total volume of catalyst present in a particular reaction system (e.g. slurry or fixed bed). Effective conditions the other oxidation reactions mentioned previously and involving hydrocarbons as feed components are known in the art.

The hydrogen peroxide production reaction of the present invention occurs in the presence of a solid catalyst. Specifically, the types of oxidation catalysts mentioned above are applicable, with a preferred catalyst being palladium dispersed on a carbon or alumina support. Since the reaction medium comprises both the organic and aqueous phases of the reaction and product solvents, respectively, the solid catalyst support should ideally be modified to achieve a suitable hydrophobic/hydrophilic balance. This allows the catalyst to reside in both the reaction and product solvent phases, so that reactants can contact the catalyst in the former phase and release oxidized product in the latter phase. A suitable hydrophobic/hydrophilic balance may be achieved by techniques known in the art, such as fluorination, which is described in U.S. Pat. No. 5,925,588 B1 for carbon supports.

When hydrogen peroxide is the oxidation product of the present invention, the aqueous product solvent is preferably an acidic solution. Of course, the particular acid used must be stable in the presence of hydrogen peroxide. Therefore, dilute inorganic acid solutions, including nitric acid, hydrochloric acid, phosphoric acid, sulfuric acid, and mixtures thereof are preferred for the product solvent. Preferably, the product solvent has a pH from about 0 to about 5.

In the case of hydrogen peroxide manufacture, hydrogen and oxygen are most advantageously mixed, from purely a chemistry standpoint and with a view toward minimizing recycle, in equimolar or stoichiometric proportions, meaning that the reactants are reacted in a ratio of 1:1 on a mole basis. Because this mixture lies well within the flammability envelope, it did not, until now, represent a practical mode of operation, as is evident in prior art methods for directly contacting hydrogen and oxygen gas where explosion hazards and/or reactant solubility limitations were problematic. As explained previously, the unique reaction environment of the present invention, whereby the reactants are dissolved in a reaction solvent having specific properties, essentially eliminates mechanisms whereby an explosion can propagate. Therefore, the process of the present invention is useful over the entire range of possible hydrogen to oxygen molar ratios, including those within the flammability envelope where the molar ratio of hydrogen to oxygen is from about 0.05 to about 15.

While the present invention, in the specific case of hydrogen peroxide production, may be used to react pure hydrogen and oxygen streams, it is also possible to react any hydrogen and oxygen containing streams available in a convenient, impure form. For example, a hydrogen feed stream may comprise a hydrogen feed component diluted with other light gases such as methane. The oxygen, of course, may be introduced as air.

The hydrogen peroxide generated according to the present invention may be further reacted to form other industrially useful products, such as propylene oxide. For example, the $H_2O_2$ direct synthesis from hydrogen and oxygen may be conveniently integrated with a process for the production of olefins and co-production of hydrogen, to yield oxidized products. Examples of olefin-generating processes are known in the art and include, for example, the dehydrogenation of $C_2$–$C_{14}$ Paraffins to olefins and hydrogen, as described in U.S. Pat. No. 4,886,928 B1, and the thermal cracking of hydrocarbons to yield unsaturated components (e.g. ethylene) and hydrogen as described in U.S. Pat. No. 4,215,231 B1.

Since these processes are capable of producing olefins, it is possible to react the hydrogen peroxide produced in the present invention with any of the effluent streams described above containing $C_2$–$C_5$ olefins, such as a paraffin dehydrogenation process effluent, a thermal cracking process effluent, and mixtures thereof to yield a $C_2$–$C_5$ oxide product (e.g. propylene oxide). Particularly attractive with this integration between processes is the ability to use the co-produced hydrogen effluent streams from the above processes as a feedstock for the $H_2O_2$ production process.

Other commercially significant end products result from downstream reactions with hydrogen peroxide. For example, oxidized aromatic compounds such as phenol are produced by reacting hydrogen peroxide with benzene, as described in U.S. Pat. No. 5,233,097 B1. Epoxides such as propylene oxide are formed by the reaction of olefins (e.g. alkenes and cycloalkenes) and hydrogen peroxide in the presence of a titanosilicate catalyst, as described in U.S. Pat. No. 5,354,875 B1. Lactones such as caprolactone are produced from the catalyzed oxidation of ketones with hydrogen peroxide in the presence of a carboxylic acid or an anhydride, as described in U.S. Pat. No. 5,665,891 B1. Finally, oximes such as cyclohexanone-oxime, a precursor to caprolactam, are formed by the ammoximation of carbonyls (e.g. cyclohexanone) with hydrogen peroxide and ammonia, as described in U.S. Pat. No. 5,227,525 B1.

In referring to the drawing, a possible reaction scheme for the production of hydrogen peroxide is depicted. The reactor 10 may be operated batchwise or in continuous mode. The reaction solvent (e.g. perfluorooctane) 12 represents a lower phase, as it is typically more dense than the product solvent (e.g. dilute sulfuric acid) 14, which has a density normally slightly above that of water. A hydrogen-containing feed and an oxygen-containing oxidizing agent are introduced separately to the reaction solvent 12 via lines 16 and 18, respectively. The dissolved reactants are contacted with a solid oxidation catalyst, residing primarily in zone A and either present as a slurry or fixed in the region of the reaction solvent/product solvent interface under the oxidation conditions mentioned previously to yield product hydrogen peroxide. Preferably, mechanical agitation, such as a stirrer 20 is used to promote this contact.

The hydrogen peroxide formed is selectively soluble in the aqueous-phase product solvent 14 and concentrates therein. Product hydrogen peroxide generated is therefore easily removed via line 22, which depicts a side stream in communication with the product solvent phase at a quiescent zone removed from the phase interface. Thus, via line 22, the reaction product hydrogen peroxide is withdrawn from the reactor 10 along with some of the aqueous-phase product solvent 14. Also contained in this side stream 22 are trace quantities of dissolved, and perhaps larger amounts of entrained, reaction solvent 12.

An economical mode of operation therefore involves separating both the reaction product and the entrained reaction solvent 12 from the product solvent 14. In the separation zone B, these purification steps are carried out. Separation of the reaction solvent 12 may be accomplished via decanting, possibly using any mechanical means known in the art (e.g. plates) to aid coalescence of liquid phases. The product is then recovered by conventional means. For instance, distillation performed as part of the separation in zone B can provide a means of separating the hydrogen peroxide product from the product solvent 14. In any case, this separation yields a regenerated product solvent, which may or may not be returned via line 24 to the product solvent phase 14 of the reactor 10.

Recovered reaction solvent that is also generated by this separation is normally most economically returned to the reaction solvent phase 12 of the reactor 10 via line 26. The purified hydrogen peroxide oxidation product is then obtained via line 28. Any small amounts of reaction solvent or product solvent lost during processing through dissolution, entrainment, vaporization, etc. can be replaced with make-up solution entering the reactor via lines 30 (for reaction solvent) and 32 (for product solvent), respectively. While the formation of a gas phase is to be avoided in the reactor itself, a purge gas, preferably nitrogen, is ideally maintained above the product 9 solvent liquid level, separated from the reactor via a stand pipe 34 leading to a liquid level control vessel 36. The purge gas enters and exits the liquid level control vessel via lines 38 and 40 to continually sweep excess reactant gases and gaseous contaminants (e.g. carbon dioxide) entering the reactor in the reactant gas streams. Without the purge, these materials would accumulate inside the reactor 10 and lead to increased reactor pressure, decreased reactor performance, and/or reduced hydrogen and oxygen solubility of the reaction solvent.

What is claimed is:

1. A process for oxidizing a feed component with air as an oxidizing agent, the process comprising dissolving the feed component and the air in a reaction solvent selected from the group consisting of fluorocarbons, chlorofluorocarbons, hydrochlorofluorocarbons, fluorine-substituted oxygenated hydrocarbons, and mixtures thereof, and thereafter reacting; the feed component and the air in the presence of a solid oxidation catalyst and under effective oxidation conditions to yield an oxidized product that is preferentially soluble in a product solvent compared to the reaction solvent.

2. The process of claim 1 where the reaction solvent, the solid oxidation catalyst, and the product solvent are contained in an oxidation reactor, and the reaction solvent and product solvent are present as separate liquid phases.

3. The process of claim 2 further comprising maintaining a gaseous environment above the reaction solvent and product solvent, where the gaseous environment has a total concentration of the oxidizing agent and the feed component of less than about 1% by volume.

4. The process of claim 1 where the feed component comprises hydrogen or a hydrocarbon selected from the group consisting of ethylene, propane propylene, n-butane, isobutane, isobutylene, tertiary butyl alcohol, orthoxylene, metaxylene, paraxylene, and mixtures thereof.

5. The process of claim 1 where the reaction solvent has an oxygen solubility of greater than about 50 ml per 100 ml of reaction solvent and a water solubility of less than about 50 ppm by weight at 1 atmosphere and 25° C.

6. The process of claim 5 where the reaction solvent is a fluorocarbon selected from the group consisting of perfluoropentane, perflouorohexane, perfluororheptane, perfluorooctane, and mixtures thereof.

7. The process of claim 1 where the product solvent comprises water or an aqueous solution.

8. The process of claim 1 where the solid oxidation catalyst comprises a solid support having dispersed thereon a metal selected from the group consisting of Au, Ag, Pt, Pd, Ir, Rh, Hg, Ru, Os, and mixtures thereof.

9. The process of claim 8 where the support is selected from the group consisting of inorganic refractory metal oxides, carbon, and polymers.

10. The process of claim 1 where the feed component comprises hydrogen, the oxidized product comprises hydrogen peroxide, and effective oxidation conditions include a temperature from about 0° C. to about 90° C. an absolute pressure from about 1 to about 200 atmospheres, a gas hourly space velocity from about 50 to about 50,000 hr$^{-1}$, and mechanical agitation.

11. The process of claim 10 where the oxidation catalyst comprises palladium dispersed on a support comprising carbon or alumina.

12. The process of claim 10 where the product solvent is an aqueous solution comprising an inorganic acid selected from the group consisting of nitric acid, hydrochloric acid, phosphoric acid, sulfuric acid, and mixtures thereof, where the product solvent has a pH from about 0 to about 5.

13. The process of claim 10 where hydrogen and oxygen are reacted in a molar ratio of hydrogen to oxygen from about 0.05 to about 15.

14. The process of claim 10 further comprising, after oxidation, reacting the hydrogen peroxide with an olefinic product stream selected from the group consisting of a paraffin dehydrogenation process effluent, a methanol-to-olefins process effluent, a thermal cracking process effluent, and mixtures thereof to yield a $C_2$–$C_5$ oxide product.

15. The process of claim 14 where the feed component is selected from the group consisting of a paraffin dehydrogenation hydrogen effluent stream, a thermal cracking process hydrogen effluent stream, and mixtures thereof.

16. The process of claim 10 further comprising, after oxidation, reacting the hydrogen peroxide with an intermediate component selected from the group consisting of aromatics, olefins, ketones, carbonyls, and mixtures thereof to yield a downstream product selected from the group consisting of oxidized aromatics, epoxides, lactones, oximes, and mixtures thereof.

17. The process of claim 16 where the intermediate component is cyclohexanone, the downstream product is cyclohexanone-oxime, and the cyclohexanone-oxime is her reacted to yield caprolactam.

18. A process for producing hydrogen peroxide, the process comprising:
   a) dissolving hydrogen and oxygen in a reaction solvent selected from the group consisting of fluorocarbons, chlorofluorocarbons, hydrochlorofluorocarbons, and mixtures thereof;
   b) reacting the dissolved hydrogen and oxygen in a reaction zone under effective oxidation conditions and in the presence of a solid oxidation catalyst to yield hydrogen peroxide, wherein effective oxidation conditions include a temperature from about 0° C. to about 90° C., an absolute pressure from about 1 to about 200 atmospheres, a gas hourly space velocity from about 50 to about 50,000 hr$^{-1}$, and mechanical agitation;
   c) extracting the hydrogen peroxide into a product solvent in which the oxidation product is preferentially soluble;
   d) separating the hydrogen peroxide and residual amounts of the reaction solvent in the product solvent from the product solvent to yield a regenerated product solvent, a purified hydrogen peroxide, and a recovered reaction solvent; and,
   e) recycling the recovered reaction solvent to the reaction zone.

19. The process of claim 18 where step (d) includes distilling or decanting the product solvent containing the hydrogen peroxide and residual amounts of reaction solvent.

20. The process of claim 18 where steps (a)–(c) occur within the reaction zone containing the reaction solvent and product solvent as separate liquid phases.

21. The process of claim 20 further comprising maintaining a purge gas stream through a gaseous environment above the reaction zone to remove gaseous contaminants entering the reaction zone with the hydrogen and the oxygen.

22. The process of claim 21 where the gaseous environment has a total concentration of the oxygen and the hydrogen of less than about 1% by volume.

23. The process of claim 21 where the purge gas stream comprises a noble gas or an inert gas selected from the group consisting of nitrogen, carbon dioxide, and mixtures thereof.

* * * * *